United States Patent [19]
Zaitlin et al.

[11] Patent Number: 5,596,132
[45] Date of Patent: Jan. 21, 1997

[54] INDUCTION OF RESISTANCE TO VIRUS DISEASES BY TRANSFORMATION OF PLANTS WITH A PORTION OF A PLANT VIRUS GENOME INVOLVING A READ-THROUGH REPLICASE GENE

[75] Inventors: Milton Zaitlin; Daniel Golemboski, both of Ithaca, N.Y.; George Lomonossoff, Norwich, England

[73] Assignee: Cornell Research Foundation, Inc., Ithaca, N.Y.

[21] Appl. No.: 488,672

[22] Filed: Jun. 7, 1995

Related U.S. Application Data

[63] Continuation of Ser. No. 198,182, Feb. 15, 1994, abandoned, which is a continuation-in-part of Ser. No. 894,064, Jun. 8, 1992, abandoned, which is a continuation-in-part of Ser. No. 491,473, Mar. 12, 1990, abandoned.

[51] Int. Cl.$^6$ .............. A01H 4/00; C12N 5/14; C12N 15/82; C12N 15/40
[52] U.S. Cl. .............. 800/205; 800/250; 800/DIG. 43; 435/320.1; 435/240.4; 435/172.3; 536/23.2
[58] Field of Search .............. 435/172.3, 320.1, 435/240.4, 235.1; 800/205, DIG. 43, 250; 536/23.2

[56] References Cited

U.S. PATENT DOCUMENTS 5,240,841  8/1993  Johnston et al. .............. 435/172.3

FOREIGN PATENT DOCUMENTS

| | | |
|---|---|---|
| 278627 | 1/1988 | European Pat. Off. . |
| 421376 | 10/1990 | European Pat. Off. . |
| 426195 | 11/1990 | European Pat. Off. . |
| 536106 | 10/1992 | European Pat. Off. . |
| WO89/08145 | 9/1989 | WIPO . |
| WO90/13654 | 11/1990 | WIPO . |
| WO91/13542 | 9/1991 | WIPO . |
| WO91/16420 | 10/1991 | WIPO . |
| WO92/03539 | 3/1992 | WIPO . |
| WO94/18336 | 8/1994 | WIPO . |

OTHER PUBLICATIONS

Inokuchi et al., "Interference with Viral Infection by Defective RNA Replicase," *Journal of Virology* 61 (12):3946–49 (1987).

Young et al., "Barley Yellow Dwarf Virus Expression in Wheat Protoplasis and Construction of Synthetic Genes to Interfere with Viral Replication," *J. Cell. Biochem.* (M552):346 (1989).

Golemboski et al., "Plants Transformed with a Tobacco Mosaic Virus Nonstructural Gene Sequence are Resistant to the Virus," *Proc. Natl. Acad. Sci. USA* 87:6311–15 (1990).

Rezaian et al., "Anti–sense RNAs of Cucumber Mosaic Virus in Transgenic Plants Assessed for Control of the Virus," *Plant Molecular Biology* 11:463–71 (1988).

Abel et al., "Delay of Disease Development in Transgenic Plants that Express the Tobacco Mosaic Virus Coat Protein Gene," *Science* 232:738–43 (1986).

Ishikawa et al., "In vitro Mutagenesis of the Putative Replicase Genes of Tobacco Mosaic Virus," *Nucleic Acids Research* 14(21):8291–05 (1986).

White et al., "In vitro Replication of Tobacco Mosaic Virus RNA in Tobacco Callus Cultures: Solubilization of Membrane–bound Replicase and Partial Purification," *Journal of Virology* 21 (2):484–92 (1977).

Beachy et al., "Characterization and In vitro Translation of the RNAs from Less–than–full–length, Virus–related, Nucleoprotein Rods Present in Tobacco Mosaic Virus Preparations," *Virology* 81:160–69 (1977).

Meshi et al., "Two Concomitant Base Substitutions in the Putative Replicase Genes of Tobacco Mosaic Virus Confer the Ability to Overcome the Effects of a Tomato Resistance Gene, Tm–1," *The EMBO Journal* 7(6):1575–81 (1988).

Powell et al., "Protection Against Tobacco Mosaic Virus in Transgenic Plants that Express Tobacco Mosaic Virus Antisense RNA," *Proc. Natl. Acad. USA* 86:6949–52 (1989).

van Dun et al., "Transgenic Tobacco Expressing Tobacco Streak Virus or Mutated Alfalfa Mosaic Virus Coat Protein Does Not Cross–protect Against Alfalfa Mosaic Virus Infection," *Virology* 164:383–89 (1988).

Carr et al., "Resistance to Tobacco Mosaic Virus Induced by the 54–kDa Gene Sequence Requires Expression of the 54–kDa Protein," *Molecular Plant–Microbe Interactions* 5(5):397–04 (1992).

J. A. Bruenn, "Relationships Among the Positive Strand and Double–strand RNA Viruses as Viewed Through Their RNA–dependent RNA Polymerases," *Nucleic Acids Research* 19(2):217–26 (1991).

Young et al., "Tobacco Mosaic Virus Replicase and Replicative Structures," *J. Cell. Sci. Suppl.* 7:277–85 (1987).

Braun et al., "Expression of Amino–terminal Portions of Full–length Viral Replicase Genes in Transgenic Plants Confers Resistance to Potato Virus X Infection," *The Plant Cell* 4:735–44 (1992).

(List continued on next page.)

*Primary Examiner*—Che S. Chereskin
*Attorney, Agent, or Firm*—Nixon, Hargrave, Devans & Doyle

[57] ABSTRACT

The invention described herein discloses a virus-induced resistance that may be transferred from one plant generation to another in which transgenic plants containing a coding sequence, taken from the read-through portion of the replicase portion of the viral genome, are resistant to subsequent disease by the virus. The use of the 54 kDa coding sequence from TMV is described as a specific example of the broader technology. Thus, the invention defines a means for bringing about viral resistance in plants which have been transformed with nucleic acid copies of fragments or segments taken from the replicase portion of the pathogenic virus genome. In addition, the present invention defines transformed plants and their seeds which carry a portion of the viral genome which codes for a portion of the read-through portion of the replicase genome of the pathogenic virus.

28 Claims, 1 Drawing Sheet

OTHER PUBLICATIONS

Lindo et al., "Pathogen–derived Resistance to a Potyvirus: Immune and Resistant Phenotypes in Transgenic Tobacco Expressing Altered Forms of a Potyvirus Coat Protein Nucleotide Sequence," *Molecular Plant–Microbe Interactions* 5(2):144–53 (1992).

Carr et al., "Resistance in Transgenic Tobacco Plants Expressing a Nonstructural Gene Sequence of Tobacco Mosaic Virus is a Consequence of Markedly Reduced Virus Replication," *Molecular Plant–Microbe Interactions* 4(6):579–85 (1991).

Anderson et al., "A Defective Replicase Gene Induces Resistance to Cucumber Mosaic Virus in Transgenic Tobacco Plants," *Proc. Natl. Acad. Sci. USA* 89:8759–63 (1992).

Young et al., "Using Plant Virus and Related RNA Sequence to Control Gene Expression," *19th Stadler Genetics Symposium* (1989).

Cuozzo et al., "Viral Protection in Transgenic Tobacco Plants Expressing the Cucumber Mosaic Virus Coat Protein or its Antisense RNA," *Bio/Technology* 6:549–57 (1988).

Audy et al., "Replicase–mediated Resistance to Potato Virus Y in Transgenic Tobacco Plants," *Molecular Plant–Microbe Interactions* 7(1):15–22 (1994).

Rizzo et al., "Nucleotide Sequence and Evolutionary Relationships of Cucumber Mosaic Virus (CMV) Strains: CMV RNA 2," *J. gen. Virol.* 69:1777–87 (1988).

Longstaff et al., "Extreme Resistance to Potato Virus X Infection in Plants Expressing a Modified Component of the Putative Viral Replicase," *The EMBO Journal* 12(2):379–86 (1993).

Gonsalves et al., "Transferring Cucumber Mosaic Virus–White Leaf Strain Coat Protein Gene into *Cucumis melo* L. and Evaluating Transgenic Plants for Protection Against Infections," *J. Amer. Soc. Hort. Sci.* 119(2):345–55 (1994).

Grumet et al., "Pathogen–derived Resistance to Viral Infection Using a Negative Regulatory Molecule," *Virology* 161:561–69 (1987).

Zaitlin et al., "Specificity of Replicase–Mediated Resistance to Cucumber Mosaic Virus," *Virology* 201:200–05 (1994).

van Dun et al., "Expression of Alfalfa Mosaic Virus cDNA1 and 2 in Transgenic Tobacco Plants," *Virology* 163:572–78 (1988).

Gonsalves et al., "Comparison of Coat Protein–mediated and Genetically–derived Resistance in Cucumbers to Infection by Cucumber Mosaic Virus Under Field Conditions with Natural Challenge Inoculations by Vectors," *Bio/Technology* 10:1564–70 (1992).

Mori et al., "Expression of Brome Mosaic Virus–encoded Replicase Genes in Transgenic Tobacco Plants," *Journal of General Virology* 73:169–72 (1992).

Rubino et al., "Resistance to Cymbidium Ringspot Tombusvirus Infection in Transgenic *Nicotiana benthamiana* Plants Expressing a Full–Length Viral Replicase Gene," *Molecular Plant–Microbe Interactions* 6(6):729–34 (1993).

Carr et al., "Replicase–mediated Resistance," *Virology* 4:339–47 (1993).

Skuzeski, J. M., et al., "Analysis of leaky viral translation termination codons *in vivo* by transient expression of improved β–glucuronidase vectors," *Plant Molecular Biology*, 15:65–79 (1990).

Zaccomer, B., et al., "The remarkable variety of plant RNA virus genomes," *Journal of General Virology*, 76:231–247 (1995).

Tenllado, F., et al., (May 1995) "*Nicotiana benthamiana* Plants Transformed with the 54 kDa Region of the Pepper Mild Mottle Tobamovirus Replicase Gene Exhibit Two Types of Resistance Responses against Viral Infection," Departamento de Biologia de Plantas, CSIC.

MacFarlane, S. A., et al., "Plants transformed with a region of the 201–kilodalton replicase gene from pea early browning virus RNA1 are resistant to virus infection," *Proc. Natl. Acad. Sci. USA*, 89:5829–5833 (1992).

Donson, J., et al., "Broad Resistance to Tobamoviruses Is Mediated by a Modified Tobacco Mosaic Virus Replicase Transgene," *MPMI*, 6(5):635–642 (1993).

Grumet, R., et al., "Pathogen–Derived Resistance to Viral Infection Using a Negative Regulatory Molecule," *Virology*, 161:561–569 (1987).

Goelet, et al. (Oct. 1982) Proc. Natl. Acad. Sci, USA 79:5818–5822.

Sulzinski, et al., (1985) Virology 145:132–140.

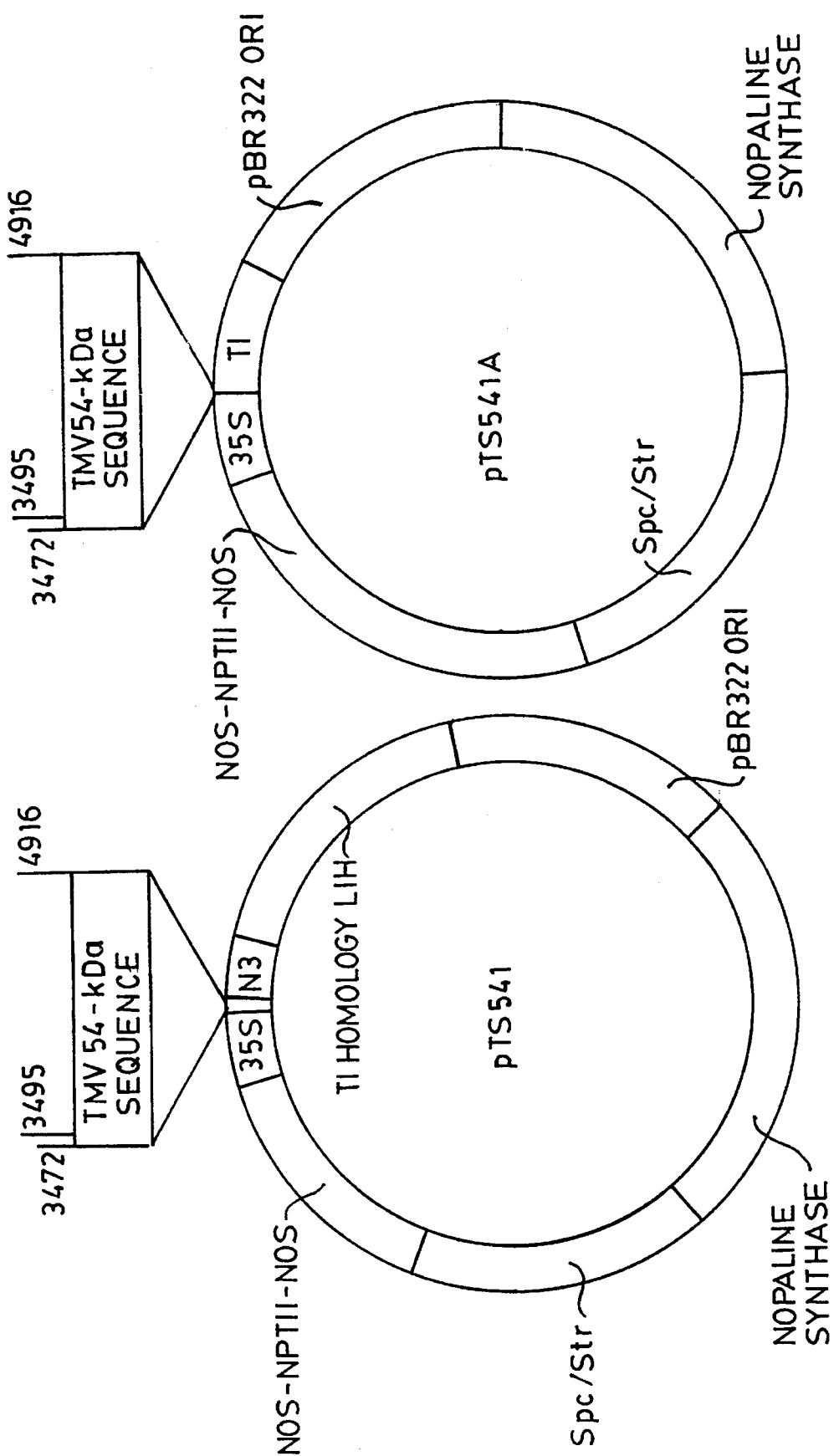

INDUCTION OF RESISTANCE TO VIRUS DISEASES BY TRANSFORMATION OF PLANTS WITH A PORTION OF A PLANT VIRUS GENOME INVOLVING A READ-THROUGH REPLICASE GENE

This application is a continuation of U.S. patent application Ser. No. 08/198,182, filed Feb. 15, 1994, now abandoned, which is a Continuation-In-Part of our previously filed U.S. patent application Ser. No. 07/894, 064 filed Jun. 8th 1992, now abandoned, which in turn is a Continuation-In-Part of our previously filed U.S. patent application Ser. No. 07/491,473, filed Mar. 12th 1990, now abandoned.

BACKGROUND OF THE INVENTION

Since the 1986 paper of P. Powell-Abel et al [see *Science* 223:738] showing that plants transformed with and expressing the coat protein gene of tobacco mosaic virus (TMV) are resistant to TMV, there have been a number of other examples of this concept which will undoubtedly have important implications for the protection of many crop species from various viral infections. To date, for example, viral coat protein-mediated resistance has been shown with at least 25 viruses in 15 taxonomic groups including alfalfa mosaic virus, tobacco rattle virus, potato virus X, cucumber mosaic virus (CMV), potyviruses, and plants transformed with both potato virus X and potato virus Y coat protein.

Plant virus sequences other than those coding for the viral coat protein have been tested to determine if transformed plants can be made to exhibit resistance to post-transformation viral infection. Positive sense sequences of alfalfa mosaic virus comprising almost full length copies of RNAs 1 and 2 failed to induce resistance in transformed plants [see Virology 163:572 (1988)]; anti-sense sequences of the TMV and potato virus coat protein genes did induce a low level of resistance in transformed tobacco [see Proc. Nat'l Acad. Sci., USA 86:6949 (1989); and EMBO Journal 7:1273 (1988)]; likewise antisense RNAs from one of three regions tested (5' sequences of RNA 1) of the CMV genome gave a low level of resistance in one transformant line.

Other forms of resistance using plant transformations with DNAs prepared from satellite RNAs of plant viruses have been reported, such as the use of the satellite of CMV [see Nature 328:799 (1987)] and the concept of the ribozyme based on sequences from satellite RNAs which possess the capacity to self cleave [see Nature 334:585 (1988)].

DESCRIPTION OF THE INVENTION

The invention described herein represents an entirely new type of virus-induced resistance which may be transferred from one plant generation to another. The present invention discloses that transgenic plants containing a coding sequence, taken from the read-through portion of the replicase portion of the viral genome, are resistant to subsequent disease by the virus; although there may be a very benign degree of virus synthesis in the inoculated leaf, the virus has been found not to spread and hence no disease develops. In the description which follows, the use of the 54 kDa coding sequence from TMV is described as a specific example of the broader technology according to the present invention. Thus, in its broadest aspects, the present invention defines a means for bringing about viral resistance in plants which have been transformed with nucleic acid copies of fragments or segments taken from the replicase portion of the pathogenic virus genome. In addition, the present invention defines transformed plants and their seeds which carry a portion of the viral genome which codes for a portion of the read-through portion of the replicase genome of the pathogenic virus. According to the present invention, transformed plants that contain a portion of the viral replicase gene within their genome are resistant to subsequent viral disease from the virus from which the portion was derived, and these plants may also be resistant to subsequent disease from other closely related viruses.

Replicase read-through as it relates to the present invention may be clearly understood with an understanding that the expression of internal open reading frames on the genomes of eukaryotic viruses is normally mediated by the synthesis of subgenomic messenger RNAs, or by processing of individual proteins from a primary polyprotein translation product. Occasionally, however, the termination codon of a gene is 'leaky' and allows for continued translation. This results in an extended protein with added amino acids at its carboxy end. In TMV, the leaky codon is UAG (amber). It has been shown that the host plants have low levels of transfer RNAs which recognize the UAG codon. A more thorough analysis of replicase read-thorugh may be found in Skuzeski et al. [see Plant Molecular Biology 15:65 (1990)].

The novel form of genetically engineered resistance to a plant virus described according to the present invention differs in several respects from the resistance engendered in transgenic plants expressing the coat protein of TMV in that resistance can be exhibited against both TMV RNA and TMV particles; resistance did not appear to break down over time or with increasing concentrations of inoculum and resistance is effective against the TMV strain from which the 54 kDa protein read-through sequence portion was obtained, but not against other tobamoviruses strains, or against other unrelated viruses. It has also been discovered that the resistance caused by the expression of the 54 kDa protein gene sequence according to the present invention acted at the level of the single cell and that it caused a very marked general suppression of virus replication. It is believed that the resistance induced by the transformation of plants with a portion of a plant virus genome involving a read-through replicase gene is not a direct result of restriction of virus movement, but that the inhibition of replication of the virus at the infection site is effective enough to prevent subsequent spread of TMV and the production of systemic disease.

In the exemplified tobacco mosaic virus description which follows, the presence of the 54 kDa TMV sequence prevents the development of local chlorosis or necrosis and any systemic development of symptoms or virus replication associated with TMV infection.

The organization of the TMV genome is well known and accepted by the scientific community. Reading from the 5' towards the 3' end of TMV RNA, open reading frames code for 126- and 183 kDa proteins, a 30 kDa movement protein, and the 17.5 kDa coat protein. However, one aspect of the genome strategy that has not been fully elucidated is the exact nature of the replicase enzyme responsible for the synthesis of the genomic and subgenomic RNAs. While it is generally accepted that the virus codes for four proteins, two of which are coded for by the genomic RNA, and two of which are coded for by individual subgenomic RNAs, it was not accepted prior to making the present that the virus codes for at least one other additional and separate protein.

N. D. Young et al reported [see J. Cell Science Supplement 7:277 (1987)] that the 5'-proximal region of the genomic RNA which encodes two coinitiated proteins, the 126 kDa and 183 kDa proteins, are components of the replicase. The 183 kDa protein is generated by a read-through of the UAG stop codon of the 126 kDa protein. The other two proteins (with known functions), the 30 kDa protein and the coat protein are each synthesized from separate subgenomic mRNAs on which each gene is 5' proximal.

What was generally not accepted prior to the making of the present invention, however, was the belief that there is a separate protein (the 54 kDa protein), for which there is an open reading frame in the read-through portion of the 183 kDa gene. The principal evidence for the existence of this protein comes from the finding that there is a third subgenomic RNA in TMV infected plants, termed $I_1$ RNA, which initiates at nucleotide residue 3405 in the TMV genome and contains the open reading frame for a 54 kDa protein [see Virology 145:132 (1985)]. Support for its function as a mRNA and as a subgenomic RNA is derived from the observation that it is found on polyribosomes and that there is a double-stranded RNA of a size corresponding to the double-stranded version of the $I_1$ subgenomic RNA [see Virology 113:417 (1981), and Virology 131:533 (1983)].

More specifically, the following sequence of the region of the TMV genome containing the read-through portion of the 183 kDa protein gene is (SEQ. NOS. 1,2 and 3)

```
      3405     3472                      3495              4919
5'-GCAGGA-CAAAGACUGGUGAUAUUUCUGAUAUG-AGUUGUUAA-3'
                                    ───              20
```

This sequence depicts a portion of the $I_1$ subgenomic RNA beginning at nucleotide residue 3405 [the complete genome of TMV is 6,395 nucleotides long and may be found in Goelet et al, Proc. Natl. Acad. Sci USA 79:5818 (1982)]. The $I_1$ RNA terminates at nucleotide 6395. In this sequence, the 54 kDa open reading frame according to the present invention extends from nucleotide residues 3495 to 4919, and the underlined region designates the sequence used for the plant transformation more fully described in the following examples.

More specifically, the gene portion for the 54 kDa protein within the $I_1$ RNA sequence is (SEQ. No. 4):

```
AUGCAG UUUUACUAUG AUAAGUGUCU CCCAGGCAAC AGCACCAUGA   46

UGAAUAAUUU UGAUGCUGUU ACCAUGAGGU UGACUGACAU UUCAUUGAAU   96

GUCAAAGAUU GCAUAUUGGA UAUGUCUAAG UCUGUUGCUG CGCCUAAGGA   146

UCAAAUCAAA CCACUAAUAC CUAUGGUACG AACGGCGGCA GAAAUGCCAC   196

GCCAGACUGG ACUAUUGGAA AAUUUAGUGG CGAUGAUUAA AAGGAACUUU   246

AACGCACCCG AGUUGUCUGG CAUCAUUGAU AUUGAAAAUA CUGCAUCUUU   296

AGUUGUAGAU AAGUUUUUUG AUAGUUAUUU GCUUAAAGAA AAAAGAAAAC   346

CAAAUAAAAA UGUUUCUUUG UUCAGUAGAG AGUCUCUCAA UAGAUGGUUA   396

GAAAAGCAGG AACAGGUAAC AAUAGGCCAG CUCGCAGAUU UUGAUUUUGU   446

AGAUUUGCCA GCAGUUGAUC AGUACAGACA CAUGAUUAAA GCACAACCCA   496

AGCAAAAAUU GGACACUUCA AUCCAAACGG AGUACCCGGC UUUGCAGACG   546

AUUGUGUACC AUUCAAAAAA GAUCAAUGCA AUAUUUGGCC CGUUGUUUAG   596

UGAGCUUACU AGGCAAUUAC UGGACAGUGU UGAUUCGAGC AGAUUUUUGU   646

UUUUCACAAG AAAGACACCA GCGCAGAUUG AGGAUUUCUU CGGAGAUCUC   696

GACAGUCAUG UGCCGAUGGA UGUCUUGGAG CUGGAUAUAU CAAAAUACGA   746

CAAAUCUCAG AAUGAAUUCC ACUGUGCAGU AGAAUACGAG AUCUGGCGAA   796

GAUUGGGUUU UGAAGACUUC UUGGGAGAAG UUUGGAAACA AGGGCAUAGA   846

AAGACCACCC UCAAGGAUUA UACCGCAGGU AUAAAAACUU GCAUCUGGUA   896
```

-continued

UCAAAGAAAG AGCGGGGACG UCACGACGUU CAUUGGAAAC ACUGUGAUCA 946

UUGCUGCAUG UUUGGCCUCG AUGCUUCCGA UGGAGAAAAU AAUCAAAGGA 996

GCCUUUUGCG GUGACGAUAG UCUGCUGUAC UUUCCAAAGG GUUGUGAGUU 1046

UCCGGAUGUG CAACACUCCG CGAAUCUUAU GUGGAAUUUU GAAGCAAAAC 1096

UGUUUAAAAA ACAGUAUGGA UACUUUUGCG GAAGAUAUGU AAUACAUCAC 1146

GACAGAGGAU GCAUUGUGUA UUACGAUCCC CUAAAGUUGA UCUCGAAACU 1196

UGGUGCUAAA CACAUCAAGG AUGGGAACA CUUGGAGGAG UUCAGAAGGU 1246

CUCUUUGUGA UGUUGCUGUU UCGUUGAACA AUUGUGCGUA UUACACACAG 1296

UUGGACGACG CUGUAUGGGA GGUUCAUAAG ACCGCCCCUC CAGGUUCGUU 1346

UGUUUAUAAA AGUCUGGUGA AGUAUUUGUC UGAUAAAGUU CUUUUUAGAA 1396

GUUUGUUUAU AGAUGGCUCU AGUUGUUAA 1425

Unfortunately, the 54 kDa protein has not been found in infected tissues. When antibodies to a β-galactosidase fusion protein for 432 amino acids specific to the read-through of the 126 kDa protein expressed in *Eschericha coli* were prepared, the 54 kDa protein in protoplast extracts could not be detected by either immunoprecipitation or Western blotting under conditions where the antibody would detect the 183 kDa protein [see T. Saito et al, Mol. Gen. Genet 205:82 (1986)]. Likewise, the 54 kDa protein has not been detectable in Western blots using antiserum made to the whole protein [see G. J. Hills et al, *Virology* 158:488 (1987)], although on occasion faint bands in the region of the gel where such a protein would be expected have been seen. The antiserum made to the whole protein is, however, capable of precipitating the 54 kDa protein generated from in vitro translation products of either TMV RNA or T7 transcripts of the 54 kDa protein gene.

In an effort to attribute a function to the 54 kDa protein, tobacco was transformed with the coding sequence for this nonstructural viral protein. Unexpectedly, these transformed plants show a complete resistance to replication in the uninoculated leaves of the U₁ strain of TMV from which the 54 kDa sequence was derived. This resistance was manifested when plants were inoculated with either high concentrations of virus or viral RNA.

In addition, the resistance exhibited by the 54 kDA transgenic plants differed in several important respects from TMV coat protein-mediated resistance: resistance was exhibited against both TMV RNA and TMV particles; it did not appear to break down over time or with increasing concentrations of innoculum; and it was effective against the TMV strain from which the 54 kDa protein gene was derived and a closely related mutant, but not against other tacamoviruses or other unrelated viruses.

Accordingly, a novel aspect of the present invention, is the conveyance of viral resistance to a plant which has previously undergone transformation of its normal genome with a portion of the replicase region of a viral genome, in its "sense" orientation.

A more complete understanding of this aspect, as well as others of the present invention. can be had by reference to the following figure and examples. With regard to the figure,

BRIEF DESCRIPTION OF THE DRAWINGS

FIG. 1 depicts plant expression vectors according to the present invention containing the TMV 54 kDa coding sequence inserted between the CaMV 35S promoter and the nopaline synthase polyadenylation site;

More specifically, FIG. 1 shows plasmids which were derived by insertion of the TMV cDNA into either the Xho I site or the Sma I site in the polylinker region of pMON316. The numbers in these vectors refer to nucleotides in the TMV genome. The NPTII gene confers a selectable kanamycin resistance marker to transformed plants; LIH refers to Ti homologous DNA; ORI refers to origin of replication

EXAMPLES

Example I (culture and maintenance of plant and virus strains)

TMV strain U₁ was purified from infected *N. tabacum* cv. Turkish Samsun plants as described by A. Asselin et al [see Virology 91:173 (1978)]. Virus RNA was isolated by phenol extraction and ethanol precipitation. *N. tabacum* cv. Xanthi nn was used as a TMV-susceptible, systemic host, and *N. tabacum* cv. Xanthi nc as a local lesion host. Plants were maintained in a greenhouse or in a growth chamber with a 14 hour per 24 hour light cycle and at 24° C.

Example II (cloning of the 54 kDa gene)

A clone of the TMV 54 kDa gene was obtained by using a 22 base oligonucleotide primer consisting of a BamH1 site linked to the 5' end of a sequence complementary to base residues 4906 to 4923 of the TMV RNA sequence. First strand DNA was synthesized by M-MLV reverse transcriptase and was rendered double stranded by sequential treatment with reverse transcriptase and Klenow relying on loop-back synthesis [see T. Maniatis et al, Molecular Cloning: A Laboratory Manual (Cold Spring Harbor, N.Y.) (1982)]. The double-stranded cDNA was digested with BamH1 and ligated into the BamH1site of M13mp18. The clones examined lacked the BamH1 site provided by the primer. This resulted in the deletion of the 54 kDa termination codon and the extension of the 54 kDa protein at its C-terminus by five amino acids. The 54 kDa insert was removed by digestion with HaeII, treated with Klenow to blunt end the 3' overhang, and finally digested with PstI. The insert was ligated into PstI/SmaI digested pBS(−) resulting in plasmid pRTT-1 which contains the TMV sequence from nucleotide residues 3472 to 4914 of the TMV RNA sequence. The orientation of the insert was such that transcription from the T7 promoter gives (+) sense transcripts as depicted in FIG. 1.

Sequencing showed that all the clones examined contained the sequence from position 3332, but lacked the BamH1 site provided by the primer. This resulted in the deletion of the 54 kDa termination codon and the extension of the 54 kDa protein at its C terminus by five amino acids derived from the vector M13mp18. The presence of an intact open reading frame was verified by insertion of the TMV sequence into a T7 transcription vector; the T7 transcript was synthesized and translated in a reticulocyte lysate system. In vitro translation yielded the desired 54 kDa product which confirmed that the AUG at position 3495 functions as an initiation codon. The product was verified as the desired 54 kDa protein by immunoprecipitation using 54 kDa antiserum.

The TMV 54 kDa sequence insert of pRTT-1 was removed by digestion with HindIII and SacI, made blunt-ended by treatment with Klenow, and ligated into either the SmaI or XhoI site of pMON316 [see S. G. Rogers et al, *Methods in Enzymology* 118:627 (1986)]. pMON316 contains a unique XhoI site in a polylinker region located between the cauliflower mosaic virus (CaMV) 35S promoter and the nopaline synthase 3'-untranslated region. A SmaI site is found in the polylinker region as well as within the Ti plasmid homologous region of pMON316. Plasmid pTS541A was generated by insertion of the TMV sequence into the SmaI site which resulted in the deletion of the nopaline synthase 3'-untranslated region and a portion of the Ti homology region. Insertion of the TMV sequence into the XhoI site resulted in the formation of pTS541. Clones containing the 54 kDa sequence in either sense or antisense orientation were characterized and isolated. Each construct was transferred to *Agrobacterium tumefaciens* GV3111 carrying pTiB6S3-SE by means of a triparental mating system [see R. T. Fraley et al, Bio/Technology 3:629 (1985)], and transconjugants were selected by resistance to kanamycin and streptomycin.

The 54 kDa coding sequence was subcloned into the plant expression vector pMON316 such that it is preceded by the CaMV 35S promoter and followed by the nopaline synthase 3' untranslated region as depicted in FIG. 1. This construct was ultimately transferred into tobacco plants by *Agrobacterium tumefaciens*-mediated leaf disk transformation. Transformants were selected on the basis of kanamycin resistance and the production of nopaline synthase. Four transformed plants were generated with pTS541 and four other plants with pTS541A which lacks the 3' nopaline synthase untranslated region and a portion of the Ti homology region located immediately downstream from the 54 kDa open reading frame. This deletion did not interfere with integration of the chimeric TMV 54 kDa gene sequence into the plant genome. Progeny seed was collected from each self-fertilized plant. Additionally, plants were transformed with the chimeric TMV gene such that 54 kDa antisense RNAs were produced. Two independent antisense transformants were selected and regenerated into mature plants.

Example III (plant transformation)

Cut pieces of sterile, TMV susceptible, *Nicotiana tabacum* cv. Xanthi nn leaves were transformed by the modified *Agrobacterium tumefaciens* GV3111 containing the TMV 54 kDa coding sequence as described by Horsch [see Science 227:1229 (1985)]. Transformed calli were selected on regeneration medium supplemented with kanamycin at a concentration of 300 µg/ml. Resistant calli were induced to regenerate shoots and roots, transferred to soil, and maintained in a greenhouse.

Example IV (nucleic acid analysis)

DNA was isolated from leaves of plants by a modified procedure of Murray and Thompson [see Nucleic Acids Research 8:4321 (1980)]. The DNA was digested with restriction enzymes, separated in 1.0% agarose gels, transferred to a nylon membrane, and hybridized to a $^{32}$P-labeled probe specific for the TMV 54 kDa sequence. RNA was isolated from leaf tissue and total RNA was separated in a 1.2% agarose gel containing formaldehyde and transferred to nitrocellulose filter paper. The blot was hybridized to a $^{32}$P-labeled probe complementary to the 54 kDa coding sequence. Six of the independently transformed plants were analyzed for expression of the chimeric gene. Genomic DNA was isolated from transformed and untransformed *N. tabacum* cv Xanthi nn. BamH 1 digests of the genomic DNA were hybridized to a $^{32}$P-labeled TMV 54 kDa sequence specific probe. Hybridization to a 3.0 kb fragment verified the presence of a full length 54 kDa coding sequence. The 54 kDa sequence insert is 1.44 kb and another 1.59 kb is contributed by flanking vector DNA. The copy number of the 54 kDa protein gene in transgenic plants, as determined by Southern analysis, varied from 1 to 5 copies per diploid genome between different transgenic plants; no copies of the 54 kDa sequence were detected in nontransformed plants nor in plants transformed with pMON316 lacking the 54 kDa sequence insert.

The TMV 54 kDa transcripts extracted from transformed plants were also examined by Northern analysis for RNA. The expected size for the chimeric MRNA of 1.6 kb was identified in total RNA from each transgenic plant. Plants containing the integrate plasmid that lacks the 3' nopaline synthase untranslated region and the Ti homologous region also synthesize a 1.6 kb transcript. In addition, a larger transcript was synthesized which might result from the lack of the termination sequence usually contributed by the nos 3' sequence. In all plants, a number of smaller unidentified transcripts were also detected. Plants transformed with the vector alone did not produce any transcripts that hybridize with the TMV 54 kDa sequence probe.

The transgenic plants were also analyzed for expression of the TMV 54 kDa protein in accordance with Example IV. When analyzed using the Western blotting or immunoprecipitation procedures described, a 54 kDa protein could not be detected from the 54 kDa transgenic plants or from protoplasts prepared from 54 kDa transgenic plants or the controls.

Example V (immunological analyses)

An antiserum to the 54 kDa protein was made by injecting rabbits with a synthetic polypeptide representing an internal region, specifically amino acid residues 164 to 179,of the 54 kDa protein. An in vitro translation product of the 54 kDa T7 transcript was immunoprecipitable with the antiserum raised against the synthetic polypeptide. For western blotting, total extracts of the transformed and untransformed plants were prepared by homogenizing leaf samples in 50 mM Tris-HCl, pH 7.5, 1% sodium dodecyl sulfate (SDS), 10 mM 2-mercaptoethanol buffer; subjected to electrophoresis in a 12.5% SDS-polyacrylamide gel; and transferred to nitrocellulose filter paper. The filter was incubated first with specific antibodies followed by gold-conjugated anti-rabbit antibodies and silver enhancement.

In studies seeking the 54 kDa protein, 1–2×50 mm TMV-infected Turkish Samsun tobacco leaf strips were vacuum infiltrated with $^{35}$S-methionine at a concentration of 10 µCi/ml in 10 mM $KH_2PO_4$ containing 1 mg/ml chloramphenicol. These were then incubated in dim light for 20 hrs at 25° C. Protoplasts were also labeled with $^{35}$S-methionine. They were prepared from *Nicotiana tabacum* cv Xanthi NN leaves. The protoplasts (about 150,000/ml containing 5 to 10 µCi/ml of $^{35}$S-methionine/ml) were incubated at 25° C. in the light for 40 hours. These were then collected by low speed centrifugation, and lysed in 20 mM Tris-HCl, pH 7.5 buffer containing 2 mM EDTA, 0.5% SDS, 0.2% β-mercapthethanol and 10 µg/ml phenylmethylsulphonyl fluoride as a protease inhibitor. Leaf strips were extracted in a mortar with a similar solution, but one which did not contain the inhibitor. The extracts were then clarified by microfuge centrifugation, and the supernatants examined for the 54 kDa protein. The presence of the 54 kDa protein was sought by incubating the extracts of the labeled leaves or protoplasts with antisera described above; an immunoprecipitation, polyacrylamide gel, and autoradiography assays were also conducted.

This antiserum was confirmed as being very active with in vitro translation products of the 54 kDa gene transcripts, and it could easily precipitate a 54 kDa protein from in vitro translation products of the RNA prepared from TMV virons containing the RNA necessary for manufacture of the 54 kDa protein. Protein could not be detected in leaves of either TMV infected plants or 54 kDa transformed plants.

Example VI (inoculation of transformed plants)

$R^1$ seedlings from self-fertilized transgenic plants were routinely inoculated with either 100 µg TMV-$U_1$ per ml of 50 mM phosphate buffer, pH 7.2, with Celite™ added as an abrasive, or TMV-$U_1$ RNA at a concentration of 300 µg/ml in pH 8.6, 50 mM Tris-phosphate buffer. Two leaves of each plant were inoculated. The volume of the inoculum was not standardized since inoculum concentration is the critical determinant as long as there is sufficient volume for adequate spread. In subsequent experiments, a closely related TMV mutant—mutant b6 as described by F. Garcia-Arenal et al, Virology 132:131 (1984) which is easier to score as a consequence of the bright yellow symptoms it elicits in the leaf. Plants were scored daily by visual observation of symptom development. In some instances, the presence of virus in inoculated plants was determined by probing leaf extracts with labeled cDNA to TMV.

In the first experiments to determine the susceptibility of the transgenic plants to infection by TMV, plants were inoculated with 50 µg TMV-$U_1$ per ml. Four rooted cuttings from each of the eight independently transformed plants containing the 54 kDa coding sequence, controls transformed with the vector alone, and several non-transformed Xanthi nn variants were inoculated. The plants were maintained in the greenhouse and monitored daily for symptom development. At 5 days post-inoculation, the transgenic controls and the non-transformed controls had clearly developed characteristic mosaic symptoms, while the transformed plants showed no sign of symptom development. No symptoms had developed on the transgenic plants by 48 days post-inoculation when the experiment was terminated. A homogenate of the inoculated and the upper leaves of those plants was used to inoculate the local lesion host, *N. tabacum* cv. Xanthi nc, to determine if a symptomless infection existed. No local lesions developed indicating the absence of detectable virus in these plants. All regenerated plants were resistant to TMV regardless of whether they were transformed with pTS541 which has the TMV sequence inserted into the complete pMON316 vector, or pTS541A which lacks the nos 3' untranslated region and the Ti homologous region. Plants transformed with the chimeric gene in the orientation which resulted in synthesis of the 54 kDa antisense RNA were not resistant to infection with TMV. However, these plants did demonstrate a delay in symptom development as compared to the vector transformed control. Since this was merely a delay in symptom development, these plants were not examined any further.

Progeny seedlings from self-fertilized transgenic plants were also analyzed for inheritability of the resistance phenomenon. R1 generation seeds were germinated on tissue culture medium containing 300 µg kanamycin per ml. Kanamycin-sensitive seedlings were considered to be those that were chlorotic and did not grow beyond the cotyledon stage. The segregation ratio of the seedlings expressing kanamycin resistance to those susceptible to kanamycin indicates that in each of the original transformants the NPTII gene was integrated at multiple loci. When seeds from self-fertilized transgenic plants were germinated on medium containing 300 µg kanamycin per ml, 95% of the seedlings emerged as being resistant to kanamycin and 5% of the seedlings became chlorotic. When transgenic seedlings were inoculated with TMV-$U_1$ at a concentration of 100 µg/ml, 24% Of these plants developed symptoms while the remaining 76% demonstrated resistance to virus infection. Thus, the resistance to TMV segregated at approximately a 3:1 ratio (resistance:susceptible) whereas the seedlings had segregated at a ratio of approximately 19:1 with respect to the resistance to kanamycin. The large number of kanamycin resistant "escapees" makes this an unreliable means of screening progeny seedlings for expressors of the integrated chimeric TMV gene. All subsequent infection experiments were done with the segregating population of line 541A11 derived R1 seedlings.

In an experiment to determine the level of resistance, seedlings were inoculated with varying concentrations of TMV. Resistance was observed at concentrations up to 500 µg of TMV per ml. The resistant plants were maintained for 30 days post-inoculation without any subsequent development of symptoms. Leaf samples were taken from the inoculated plants to assay for virus replication and spread of virus. Extracts of the leaf samples were probed with cDNA prepared from purified TMV RNA. Virus could not be detected in either the inoculated leaves nor in the systemic leaves of the plants that demonstrated resistance, indicating that there is no viral replication in the resistant plants and that the resistance is absolute and not just a suppression of symptom development resulting in an asymptomatic spread of the virus throughout the plant. Transgenic plants containing the vector alone without the TMV sequence and non-transformed plants were used as controls, and virus was easily detectable in both types of control plants as well as in the progeny segregants that developed symptoms.

As a final evaluation of the resistance to viral infection of the transgenic plants, some plants were transferred immediately after inoculation to a growth chamber maintained at 31° C., to determine if the 54 kDa-induced resistance to TMV is temperature sensitive. Of the seven inoculated plants which carry the 54 kDa gene sequence, five did not develop symptoms at 31° C. whereas all control plants developed symptoms typical to those kept at 24° C.

In conclusion, the preceding description has demonstrated the novel aspect of the present invention that transgenic plants containing a coding sequence replicase read-through portion of a viral genome associated with the replicase region of the virus are resistant to infection with the virus from which the portion was initially obtained.

When compared with viral coat induced resistance, a number of advantages are present in the present invention. For example, the resistance to viral infection utilizing a replicase related coding sequence as described in the present invention is not as "fragile" as coat protein-induced resistance in which resistance may break down when high concentrations of inoculum are used. In contrast, with the present invention, complete resistance is observed in non-inoculated leaves of plants challenged with high concentrations of virus or viral RNA. Whereas the protection mediated by the coat proteins of TMV and AlMV can be overcome by inoculating with viral RNA, the induced resistance according to the present invention utilizing the 54 kDa code sequence remains uncompromised when challenged with viral RNA. The level of resistance in 54 kDa transgenic plants does not appear to be due to the level of expression: plants with only one copy of the gene sequence did not show a decrease in resistance to intact virions or viral RNA. A single copy of the TMV coat protein is also sufficient to protect the plant whereas one copy of the AIMV coat protein is not.

In addition to the above, studies were also conducted which were aimed at discovering the stage at which the virus life cycle is disrupted using a portion of the replicase genome according to the present invention.

Example VII

Tobacco plants (*Nicotiana tabacum L*), cv. Xanthi nn, as well as the 54 kDa transgenic Xanthi nn, and the TMV local lesion indicator host Xanthi NN, were maintained under greenhouse conditions. Plants used for protoplast preparation were transferred to a growth chamber on a 14 hr light/10 hr dark cycle at 24° C. for at least one week prior to use. The light intensity was reduced to 125–150 $\mu E \cdot m^{-2} \cdot s^{-1}$ by shading with cheese cloth. TMV strains U1 and U2 [see Phytopathology 44:277 (1954)] were purified [see Virology 91:133 (1978)]. The TMV strain U1 used in some of the following examples was derived from transcripts generated from a full length cDNA clone of the virus. Virus infection of whole plants was achieved by inoculation of both upper and lower surfaces of fully expanded Xanthi nn or 54 kDa transgenic tobacco leaves with 0.05, 0.5. or 1.0 mg/ml of TMV strain U1 in 0.05M potassium phosphate, pH 7.0 buffer, with Celite as an abrasive. Viral RNA was prepared from TMV strains U1 and U2 by phenol extraction and ethanol precipitation.

Example VIII (protoplast preparation and infection)

Protoplasts were obtained from leaves of 54 kDa transgenic plants and control, nontransgenic tobacco plants. The protoplasts (0.5–1.0×10⁶ cells/ml) were infected by electroporation with viral RNA extracted from TMV strains U1 or U2. Electroporation was performed in a final volume of 2 ml of sterile 0.7 ml of sterile 0.7M mannitol, using a single ring electrode (2.5 mm high, 1 cm gap) connected to a Progenetor 1 electroporation apparatus by applying two 5 msec pulses of 300 V. The viral RNA concentrations ranged from 10 to 100 µg/ml although routinely 10 µg/ml was used. In addition, all experiments included a set of mockinoculated protoplasts electroporated in buffer alone.

After electroporation, protoplasts were resuspended in incubation medium: 0.7M mannitol containing 1 mM $KNO_3$, 1 mM $MgSO_4$, 0.1 mM $CaCl_2$, 1 µM KI, 0.01 µM $CuSO_4$, 10 µg/ml rimocidin, and 100 µg/ml carbenicillin buffered with 50 mM citrate, pH 5.5 buffer. The protoplasts (3 ml) were transferred to agar plates (1% noble agar in incubation medium prepared in 60–×15–mm petri dishes) and incubated in low light at 25° C. [see Virology 161:488 (1987)].

Example IX (analysis of protoplast proteins)

Accumulation of TMV coat protein in protoplasts was detected by western blotting. Protoplasts were harvested by low speed centrifugation and disrupted in 50–100 µl of SDS—polyacrylamide gel electrophoresis (PAGE) sample buffer [see Nature 227:680].

The released proteins were separated by SDS-PAGE, electoblotted to nitrocellulose, and probed using a rabbit polyclonal antiserum (diluted 1:1,000) to strain U1 TMV coat protein and [$^{125}$I] protein A. To monitor the synthesis of virus-encoded proteins in protoplasts, L-[$^{35}$S] methionine was added to the incubation medium at a concentration of 10 µCi/ml. After continuous labeling, protoplasts were washed in 0.7 ml mannitol and disrupted in buffer. [$^{35}$S]-labeled proteins were analyzed by SDS-PAGE [see Nature 227:680 (1970)] and autoradiography.

Example X (analysis of RNA)

At various times after electroporation, protoplasts were harvested, washed in sterile 0.7M mannitol, disrupted in 50 mM Tris HCl, pH 8.0 buffer, 10 mM EDTA, 2% SDS, and extracted with phenol/chloroform/isoamyl alcohol (50:50:1). In some instances, following ethanol precipitation, lithium chloride-soluble (enriched in ds RNA) and lithium chloride-insoluble (enriched in ss RNA) fractions were prepared [see Mol. Cell. Bio. 5:2238 (1985)]. Leaf RNA was prepared in the same manner starting with leaf tissue pulverized in liquid nitrogen.

RNAs were separated on formaldehyde-containing, 1.2% agarose gels and were blotted to nitrocellulose, which was then probed with in vitro-synthesized, [$^{32}$P]-labeled, ssRNA transcripts. Northern blots were prehybridized and hybridized for 24 hrs at 45° C. in 5× SSC (1× SSC=0.15M sodium chloride, 0.015M sodium citrate, pH 7.0), 5×Denhardt's solution, 50 mM sodium phosphate, pH 7.0, 0.1% SDS, 250 µg/ml of yeast RNA, and 50% formamide, and were washed five times in 0.1×SSC, 0.2% SDS at 65° C. Relative amounts of specifically hybridizing RNA bands were qualified by excising the appropriate areas of the nitrocellulose filter using an autoradiograph as a template and determining the amount of radioactive probe bound using a liquid scintillation spectrometer.

In vitro-synthesized RNA probes were prepared from two DNA templates: 1) T3 polymerase transcription [see Molecular Cloning, Cold Spring Harbor Laboratories (1989)] of pBS126, a derivative of pBSM13-containing an insert corresponding to nucleotides 1–3,785 of strain U1

TMV, including the whole of the 126 kDa protein reading frame, yields a (+) sense transcript corresponding to this region of TMV genomic RNA and complementary to the 3' region of full length (−) sense TMV RNA; 2) SP6 polymerase transcription [see Molecular Cloning, Cold Spring Harbor Laboratories (1989)] of pSP64 derivative containing an insert corresponding to the coat protein gene of TMV (from nucleotide 5,663 to the 3' end). This yields a (−) sense transcript complementary to the (+) sense, full length, as well as the subgenomic TMV RNAs, all of which possess the same 3' terminus. Additionally, T7 transcripts of pRTT-1, containing the sequence encoding the strain U1 TMV 54 kDa protein were prepared and used to program wheat-germ [see PNAS (USA)70:2330 (1973)] and reticulocyte lysate-derived [see Eur. J. Biochem. 67:247 (1976)], in vitro translation systems.

The protoplasts from the 54 kDa transgenic plants (see Example VIII) that were electroporated 24 or 48 hrs earlier with strain UI TMV RNA did not contain any infectious virus detectable by bioassay on local lesion indicator plants, but under the same experimental conditions, these protoplasts replicated infectious strain U2 TMV. In contrast, control protoplasts from nontransformed plants replicated both strains of TMV. According to bioassay data, protoplasts derived from 54 kDa transgenic plants remained resistant to strain U1 TMV RNA even when the inoculum concentration was increased from 10 to 100 µg/ml of RNA. Consistent with bioassay data, western blot analysis of protoplast proteins showed that 54 kDa transgenic protoplasts accumulated no detectable strain U1 TMV coat protein, although under the same conditions these cells accumulated strain U2 TMV coat protein in amounts similar to those in the control, nontransgenic tobacco protoplasts.

These results indicate that the resistance displayed by whole, intact 54 kDa transgenic plants according to the present invention is retained by protoplasts prepared from them, and that the resistance mechanism functions at the level of the single cell. This implies that resistance at the whole plant level is not due primarily to a block in cell-to-cell or long distance virus spread, but must act either by preventing the initiation of virus infection or by inhibiting virus replication once infection has taken place. This conclusion is consistent with data showing that plasmodesmata (the routes of cell to cell virus spread) in 54 kDa transgenic plants appear to be unmodified and have normal molecular exclusion limits.

The 126 kDa protein is the more abundant of the two known viralcoded TMV replicase components and its synthesis, directed by the 5' proximal open reading frame of TMV genomic RNA is probably the first step in replication after (or during) virus uncoating. The 126 kDa protein was not apparent among [$^{35}$S]-labeled proteins extracted from 54 kDa transgenic protoplasts infected with strain U1 TMV. However, under the same conditions the 126 kDa protein was present in extracts of [$^{35}$S]-labeled protein from nontransgenic tobacco protoplasts infected with strain U1 TMV. The equivalent, faster moving protein encoded by strain U2 TMV was synthesized in both transgenic and nontransgenic protoplasts infected with that strain of TMV. Similarly, synthesis of strain U2 TMV coat protein was observed in both cell types. Synthesis of strain U1 TMV coat protein could not be observed in this way because it lacks methionine. Attempts to improve the sensitivity of detection of the 126- and 183 kDa proteins by immunoprecipitation with appropriate antisera were unsuccessful.

Although direct methods were not successful to demonstrate the synthesis of viral-coded replicase proteins in 54 kDa transgenic tobacco protoplasts infected with strain U1 TMV, there remained an indirect way of detecting the presence of these proteins. Specifically, any products of replicase activity will betray the presence of small levels of all of the replicase components. Because the initial product of replication is (−) sense RNA generated from the input, (+) sense, genomic TMV RNA, RNA from strain U1 TMV-infected 54 kDa transgenic tobacco protoplasts was probed for the presence of full length (−) sense TMV RNA. By 21 hrs post-inoculation, trace amounts of ss, (−) sense, full length TMV RNA were found to be present in the strain U1 TMV-infected 54 kDa transgenic tobacco protoplasts, although its ds form was not detectable. Therefore, some small quantity of virus-coded replicase components must have been synthesized after infection and must have been functional to some extent in these cells.

Detection of (−) sense TMV RNA in the 54 kDa transgenic tobacco protoplasts prompted the study to determine if replication proceeded beyond (−) strand synthesis and resulted in any (+) strand synthesis. Northern analysis of protoplast RNAs with a probe specific for (+) sense, 3' sequences of TMV RNA detected the presence of low levels of (+) sense TMV RNAs by 5 hours post-inoculation and the full complement of full length and subgenomic TMV RNAs by 21 hours post-inoculation in strain U1 TMV-infected 54 kDa transgenic tobacco protoplasts. The full complement of ds forms of the full length and subgenomic TMV RNAs were also observed in the TMV-infected nontransgenic protoplasts. However, northern blot analysis was not sensitive enough to detect TMV dsRNAs in the TMV-infected 54 kDa transgenic protoplasts. Counting of the radioactive probe bound to specific ssRNA bands showed that the levels of full length (+) sense TMV RNAs which accumulated in strain U1 TMV-infected 54 kDa transgenic tobacco protoplasts, were between 20- and 80-fold less than those in infected nontransgenic protoplasts depending on the specific experiment. Similar results were obtained either the laboratory U1 strain TMV RNA or clone-derived U1 TMV RNA were used. The results indicate, therefore, that a low level of strain U1 TMV replication can occur in 54 kDa transgenic tobacco protoplasts.

The studies described in the above examples, particularly Examples VII–X, of 54 kDa transgenic tobacco protoplasts with strain U1 TMV indicated that these cells permit the synthesis of trace amounts of TMV-specific RNAs. Next examined was whether the results obtained with protoplasts truly reflected the characteristics of the resistance phenomenon in leaf cells of whole 54 kDa transgenic plants. To do this, leaves of 54 kDa transgenic tobacco plants were inoculated on their upper and lower surfaces with strain U1 TMV particles at concentrations of 0.05 and 0.5 mg/ml. These highly concentrated inocula (two and three orders of magnitude greater than those typically employed to infect nontransgenic tobacco plants) were used to maximize the number of leaf cells infected and thus increase the chances of detecting virus-specific RNAs.

Northern blot analysis of RNA from 54 kDa transgenic tobacco leaves inoculated with strain U1 TMV at 0.05 mg/ml did not reveal any viral RNAs. However, increasing the inoculum to 0.5 mg/ml resulted in the production of detectable levels of full length and sub-genomic (+) sense TMV RNAs, which increased over time. Once again, any TMV double-stranded RNAs that may have been present were at levels too low to detect using this methodology. Comparison of the amounts of radioactive probe bound to specific RNA bands in Northern blots indicated that the levels of full length (+) sense TMV RNAs that accumulate in heavily inoculated 54 kDa transgenic tobacco leaves were 17- to 20-fold less than those found in nontransgenic tobacco tissue. Similar results were obtained both with laboratory virus isolate and with virus propagated from an infectious TMV cDNA clone (applied at a concentration of 1 mg/ml). When the heavily inoculated areas of 54 kDa transgenic tobacco leaves were used as sources of inoculum for assay on local lesion indicator plants, small amounts of biologically active virus were sometimes detected. No virus was detectable in other leaves of the same plant or on uninoculated parts of the same leaf when clone-derived virus was used as the inoculum.

Overall, the results obtained with heavily inoculated 54 kDa transgenic tobacco leaves appear consistent with those obtained using protoplasts in that there appears to be a major inhibition, although not a complete shutdown, of virus replication.

There are two possibilities to describe how the inhibition of replication of strain U1 TMV is achieved in 54 kDa transgenic tobacco plants according to the present invention. First, the 54 kDa protein or its RNA might directly inhibit replicase activity, or second, the 54 kDa protein or its RNA may act indirectly, for instance by inhibiting synthesis of the virus-coded replicase components, the 126- and 183 kDa proteins. The second possibility was addressed by translating TMV RNA in rabbit reticulocyte or wheat-germ in vitro translation systems that had also been programmed or pre-programmed with an in vitro-synthesized DNA transcript encoding the 54 kDa protein. In both of these cell-free translation systems, synthesis of the 126- and 183-, as well as the 54 kDa proteins occurred with no suggestion of specific inhibition of 126- or 183 kDa protein synthesis. Thus, there is no evidence that the 54 kDa protein or its RNA according to the present invention, affect the synthesis of virus-coded replicase components. The results are, therefore, consistent with the first possibility, namely that the 54 kDa protein or its corresponding RNA affect replicase activity directly.

In subsequent investigations conducted by the inventors and reported in Molecular Plant-Microbe Interactions 5:397 (1992), the disclosure of which is incorporated in toto herein, into the present invention it was confirmed that when host cells were transformed with protoplast constructs capable of generating full-length transcripts corresponding to the 54 kDa gene sequence, only those constructs with the potential to direct synthesis of full-length or close-to-full-length 54 kDa proteins conferred resistance to TMV. This strongly indicates that expression of the 54 kDa protein gene sequence at the RNA level alone is insufficient for resistance, and implies a role for the 54 kDa protein in resistance.

In a related plant host system, that of pea early browning virus (whose genome is known and reported in the literature, for example, in Proc. Natl. Acad. Sci. U.S.A. 89:5832), only plants transformed with a DNA construct containing an intact open reading frame (nucleotides 4013 to 5425) for the viral 54 kDa protein were found to be resistant to challenge by the virus, whereas plants transformed with inadvertently mutated sequences incapable of synthesizing intact 54 kDa protein were not resistant. This finding is also consistent with the belief that the 54 kDa-mediated resistance according to the present invention described herein requires the participation of the open reading frame translation product interacting, perhaps, with viral RNA or binding to and interfering with some part of the replication machinery.

Given the similarities between the genome organizations of pea early browning virus and TMV, it would seem likely that the model which best describes resistance to TMV would also explain resistance to the pea early browning virus.

In conclusion, the data reported herein clearly indicate that transgenic tobacco plants transformed with a 54 kDa gene encoded in the read-through portion of the replicase protein also exhibit TMV resistance. In the invention described herein, replicase sequences are used for the plant transformation. Although the two systems exemplified herein, both of which involve transformation with viral replicase sequences, may operate by different mechanisms, it appears that this replicase-mediated resistance is generic and applicable to other plants and their pathogenic viruses, in which a replicase read-though is used to transfer resistance to viral diseases.

Thus, while we have illustrated and described the preferred embodiment of our invention, it is to be understood that this invention is capable of variation and modification, and we therefore do not wish or intend to be limited to the precise terms set forth, but desire and intend to avail ourselves of such changes and modifications which may be made for adapting the present invention to various usages and conditions. Accordingly, such changes and modifications are properly intended to be within the full range of equivalents, and therefore within the purview of the following claims. The terms and expressions which have been employed in the foregoing specification are used therein as terms of description and not of limitation, and thus there is no intention, in the use of such terms and expressions, of excluding equivalents of the features shown and described, or portions thereof, it being recognized that the scope of the invention is defined and limited only by the claims which follow.

Among such modifications are, for example, the substitution of plant transformation vectors other than those specified in the examples above. For example, vectors which are within the range of substitutes or equivalents are those such as pBIN19, pBI101, pROK1, pROK$_2$, pAGS135, pARC12, PGA470, pRAL3940, and pCT1T3, among others. The present invention has been exemplified with TMV and another plant virus, pea early browning virus (in which transformation of Nicotiana benthamiana plants with an analogous 54 kDa protein sequence to the TMV described in detail above) render the plants highly resistant to the virus. Other viruses such as tobacco rattle virus, carnation mottle virus, pepper mild mottle virus, tomato bushy stunt virus, and other members of the tobamovirus, tobravirus, tombusvirus and carmovirus groups which also contain viral replicase read-through regions within their genomes are also encompassed by the present invention, as are the host plants transformed with genetic sequences related to the replicase portions of these viruses. Since it is known that similarities in sequences exist between the replicase (polymerase) regions of RNAs of many "unrelated" plant viruses [see for example, N. Habili et al., Nucleic Acids Research 17:9543 (1989)], including similarities between certain plant and animal RNA viruses, these are properly considered to be equivalents and therefore encompassed by the scope of the present invention.

The listing of all nucleic acid and amino acid sequences contained in this disclosure are reproduced in the following Sequence Listing:

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
      ( A ) LENGTH: 6 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:1:

GCAGGA 6

( 2 ) INFORMATION FOR SEQ ID NO:2:

( i ) SEQUENCE CHARACTERISTICS:
      ( A ) LENGTH: 26 base pairs
      ( B ) TYPE: nucleic acid
      ( C ) STRANDEDNESS: single
      ( D ) TOPOLOGY: linear ( i i ) MOLECULE TYPE: RNA ( x i ) SEQUENCE DESCRIPTION: SEQ ID NO:2:

CAAAGACUGG UGAUAUUUCU GAUAUG 26

( 2 ) INFORMATION FOR SEQ ID NO:3:

( i ) SEQUENCE CHARACTERISTICS:
      ( A ) LENGTH: 9 base pairs
      ( B ) TYPE: nucleic acid
      ( C ) STRANDEDNESS: single
      ( D ) TOPOLOGY: linear ( i i ) MOLECULE TYPE: RNA ( x i ) SEQUENCE DESCRIPTION: SEQ ID NO:3:

AGUUGUUAA 9

( 2 ) INFORMATION FOR SEQ ID NO:4:

( i ) SEQUENCE CHARACTERISTICS:
      ( A ) LENGTH: 1425 base pairs
      ( B ) TYPE: nucleic acid
      ( C ) STRANDEDNESS: single
      ( D ) TOPOLOGY: linear ( i i ) MOLECULE TYPE: RNA ( x i ) SEQUENCE DESCRIPTION: SEQ ID NO:4:

| | | | | | |
|---|---|---|---|---|---|
| AUGCAG | UUUUACUAUG | AUAAGUGUCU | CCCAGGCAAC | AGCACCAUGA | 46 |
| UGAAUAAUUU | UGAUGCUGUU | ACCAUGAGGU | UGACUGACAU | UUCAUUGAAU | 96 |
| GUCAAAGAUU | GCAUAUUGGA | UAUGUCUAAG | UCUGUUGCUG | CGCCUAAGGA | 146 |
| UCAAAUCAAA | CCACUAAUAC | CUAUGGUACG | AACGGCGGCA | GAAAUGCCAC | 196 |
| GCCAGACUGG | ACUAUGGAA | AAUUUAGUGG | CGAUGAUUAA | AAGGAACUUU | 246 |
| AACGCACCCG | AGUUGUCUGG | CAUCAUUGAU | AUUGAAAAUA | CUGCAUCUUU | 296 |
| AGUUGUAGAU | AAGUUUUUUG | AUAGUUAUUU | GCUUAAAGAA | AAAAGAAAAC | 346 |
| CAAAUAAAAA | UGUUUCUUUG | UUCAGUAGAG | AGUCUCUCAA | UAGAUGGUUA | 396 |

```
GAAAAGCAGG  AACAGGUAAC  AAUAGGCCAG  CUCGCAGAUU  UUGAUUUUGU              446

AGAUUUGCCA  GCAGUUGAUC  AGUACAGACA  CAUGAUUAAA  GCACAACCCA              496

AGCAAAAAUU  GGACACUUCA  AUCCAAACGG  AGUACCCGGC  UUUGCAGACG              546

AUUGUGUACC  AUUCAAAAAA  GAUCAAUGCA  AUAUUUGGCC  CGUUGUUUAG              596

UGAGCUUACU  AGGCAAUUAC  UGGACAGUGU  UGAUUCGAGC  AGAUUUUUGU              646

UUUUCACAAG  AAAGACACCA  GCGCAGAUUG  AGGAUUUCUU  CGGAGAUCUC              696

GACAGUCAUG  UGCCGAUGGA  UGUCUUGGAG  CUGGAUAUAU  CAAAAUACGA              746

CAAAUCUCAG  AAUGAAUUCC  ACUGUGCAGU  AGAAUACGAG  AUCGGCGAA               796

GAUUGGGUUU  UGAAGACUUC  UUGGGAGAAG  UUUGGAAACA  AGGGCAUAGA              846

AAGACCACCC  UCAAGGAUUA  UACCGCAGGU  AUAAAAACUU  GCAUCUGGUA              896

UCAAAGAAAG  AGCGGGGACG  UCACGACGUU  CAUUGGAAAC  ACUGUGAUCA              946

UUGCUGCAUG  UUUGGCCUCG  AUGCUUCCGA  UGGAGAAAAU  AAUCAAGGA               996

GCCUUUUGCG  GUGACGAUAG  UCUGCUGUAC  UUUCCAAAGG  GUUGUGAGUU              1046

UCCGGAUGUG  CAACACUCCG  CGAAUCUUAU  GUGGAAUUUU  GAAGCAAAAC              1096

UGUUUAAAAA  ACAGUAUGGA  UACUUUUGCG  GAAGAUAUGU  AAUACAUCAC              1146

GACAGAGGAU  GCAUUGUGUA  UUACGAUCCC  CUAAAGUUGA  UCUCGAAACU              1196

UGGUGCUAAA  CACAUCAAGG  AUUGGGAACA  CUUGGAGGAG  UUCAGAAGGU              1246

CUCUUUGUGA  UGUUGCUGUU  UCGUUGAACA  AUUGUGCGUA  UUACACACAG              1296

UUGGACGACG  CUGUAUGGGA  GGUUCAUAAG  ACCGCCCCUC  CAGGUUCGUU              1346

UGUUUAUAAA  AGUCGGUGA   AGUAUUUGUC  UGAUAAAGUU  CUUUUUAGAA              1396

GUUUGUUUAU  AGAUGGCUCU  AGUUGUUAA                                       1425
```

Having thus described our invention and the manner and process of making and using it in such full, clear, concise, and exact terms so as to enable any person skilled in the art to which it pertains, or to with which it is most nearly connected, to make and use the same,

We claim:

1. An isolated DNA molecule encoding a protein or polypeptide segment of a replicase for a plant pathogenic virus, wherein the plant pathogenic virus genome coding for the replicase includes a coding region for a replicase read through portion and, wherein the segment of the replicase is in the replicase read through portion.

2. An isolated DNA molecule according to claim 1 wherein the plant pathogenic virus is selected from the group consisting of tobravirus, tobamovirus, tombusvirus, and carmovirus.

3. An isolated DNA molecule according to claim 2, wherein the plant pathogenic virus is selected from the group consisting of tobacco mosaic virus, pea early browning virus, tobacco rattle virus, carnation mottle virus, pepper mild mottle virus, and tomato bushy stunt virus.

4. An isolated DNA molecule according to claim 3, wherein the plant pathogenic virus is tobacco mosaic virus and the protein or polypeptide segment has a molecular weight of about 54 kDa.

5. An isolated DNA molecule according to claim 4, wherein the protein or polypeptide segment is the same as that corresponding to SEQ. ID. No. 4.

6. An expression vector containing the DNA molecule of claim 1.

7. An expression vector according to claim 6, wherein the DNA molecule is present in the expression vector in proper sense orientation and correct reading frame.

8. An expression vector according to claim 6, wherein the plant pathogenic virus is selected from the group consisting of tobravirus, tobamovirus, tombusvirus, and carmovirus.

9. An expression vector according to claim 8, wherein the plant virus is tobacco mosaic virus and the protein or polypeptide segment has a molecular weight of about 54 kDa.

10. A plant cell containing the DNA molecule according claim 1.

11. A plant cell according to claim 10, wherein the plant pathogenic virus is selected from the group consisting of tobravirus, tobamovirus, tombusvirus, and carmovirus.

12. A plant cell according to claim 11, wherein the plant pathogenic virus is tobacco mosaic virus and the protein or polypeptide segment has a molecular weight of about 54 kDa.

13. A plant cell according to claim 10, wherein the DNA molecule is in an expression system.

14. transformed with the DNA molecule according to claim 1.

15. A plant according to claim 14, wherein the plant pathogenic virus is selected from the group consisting of tobravirus, tobamovirus, tombusvirus, and carmovirus.

16. A plant according to claim 15, wherein the plant pathogenic virus is tobacco mosaic virus and the protein or polypeptide segment has a molecular weight of about 54 kDa.

17. A plant according to claim 16, wherein the protein or polypeptide segment is the same as that formed by translation of the nucleic acid sequence corresponding to SEQ. ID No. 4.

18. A plant seed containing the DNA molecule of claim 1.

19. A plant seed according to claim 18, wherein the plant pathogenic virus is selected from the group consisting of tobravirus, tobamovirus, tombusvirus, and carmovirus.

20. A method of imparting disease resistance to plants comprising:

transforming a plant cell with the DNA molecule according to claim 1.

21. A method according to claim 20 further comprising:

propagating a plant from said plant cell after said transforming.

22. A method according to claim 20, wherein the plant pathogenic virus is selected from the group consisting of tobravirus, tobamovirus, tombusvirus, and carmovirus.

23. A method according to claim 20, wherein said transforming comprises:

infecting the plant cell with *Agrobacterium tumefaciens* containing the DNA molecule.

24. An isolated RNA molecule encoding a protein or polypeptide segment of a replicase for a plant pathogenic virus, wherein the plant pathogenic virus genome coding for the replicase includes a coding region for a read through portion and, wherein the segment of the replicase is in the replicase read through portion.

25. An isolated RNA molecule according to claim 24, wherein the plant pathogenic virus is selected from the group consisting of tobravirus, tobamovirus, tombusvirus, and carmovirus.

26. An isolated RNA molecule according to claim 24, wherein the plant pathogenic virus is selected from the group consisting of tobacco mosaic virus, pea early browning virus, tobacco rattle virus, carnation mottle virus, pepper mild mottle virus, and tomato bushy stunt virus.

27. An isolated RNA molecule according to claim 26, wherein the plant pathogenic virus is tobacco mosaic virus and the protein or polypeptide segment has a molecular weight of about 54 kDa.

28. An isolated RNA molecule according to claim 27, wherein the RNA molecule has a nucleic acid sequence corresponding to SEQ. ID. No. 4.

* * * * *